United States Patent [19]

Shetty et al.

[11] Patent Number: 5,057,108
[45] Date of Patent: Oct. 15, 1991

[54] METHOD OF SURFACE FINISHING ORTHOPEDIC IMPLANT DEVICES

[75] Inventors: H. Ravindranath Shetty, Warsaw; John H. Hiss, Leesburg; Kevin M. Greig, Warsaw, all of Ind.

[73] Assignee: Zimmer, Inc., Warsaw, Ind.

[21] Appl. No.: 464,096

[22] Filed: Jan. 12, 1990

[51] Int. Cl.$^5$ .......................... A61F 5/04; B21S 51/28
[52] U.S. Cl. ......................................... 606/53; 72/53
[58] Field of Search ..................... 606/53, 69, 101, 78; 72/53, 54

[56] References Cited

U.S. PATENT DOCUMENTS

| | | | |
|---|---|---|---|
| 3,073,022 | 1/1963 | Bush | 72/53 |
| 3,531,964 | 10/1970 | Manning, Jr. | 72/53 |
| 3,754,976 | 8/1973 | Babaki | 72/53 |
| 4,135,283 | 1/1979 | Kohlhage | 72/53 |
| 4,226,111 | 10/1980 | Wahli | 72/53 |
| 4,581,913 | 4/1986 | Reed | 72/53 |
| 4,612,920 | 9/1986 | Lower | 606/66 |

FOREIGN PATENT DOCUMENTS 166423 3/1980 Japan.
525371 11/1977 U.S.S.R.

OTHER PUBLICATIONS

Glass Bead Impact Blasting, Michael Woelfel and Robert Mulhall, Sep. 1982, Metal Progress, vol. 122, No. 4, pp. 57–59.

Primary Examiner—Danton D. DeMille
Assistant Examiner—Michael Brown
Attorney, Agent, or Firm—Paul D. Schoenle

[57] ABSTRACT

A surface treatment process for stainless steel orthopedic implant devices and an orthopedic implant device surface treated in accordance with the disclosed process are disclosed. A rough ground or machined stainless steel part is shot blasted with stainless steel shot. The device is then shot blasted with glass beads having a nominal size of between one-tenth and one-half that of the stainless steel shot. Electropolishing and passivation follow the shot blasting steps. A part thus treated includes a heavily cold-worked outer layer that enhances the fatigue properties of the stainless steel orthopedic implant device.

9 Claims, 2 Drawing Sheets

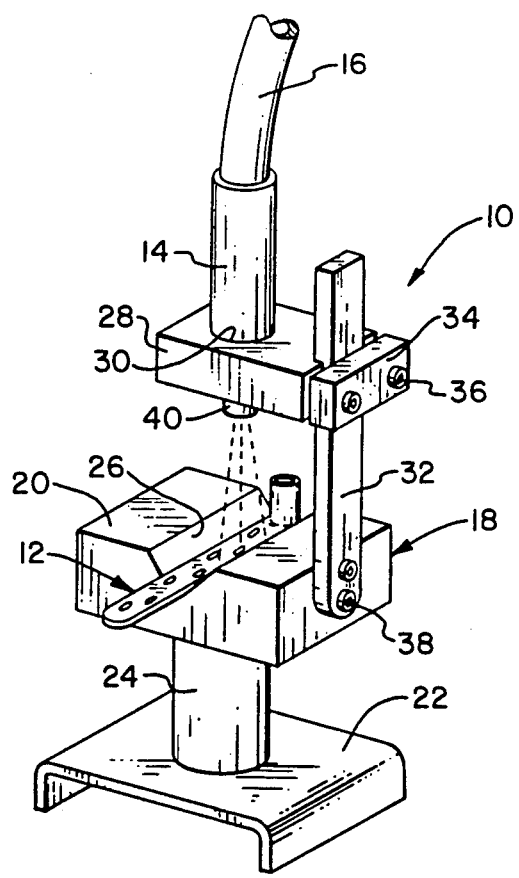
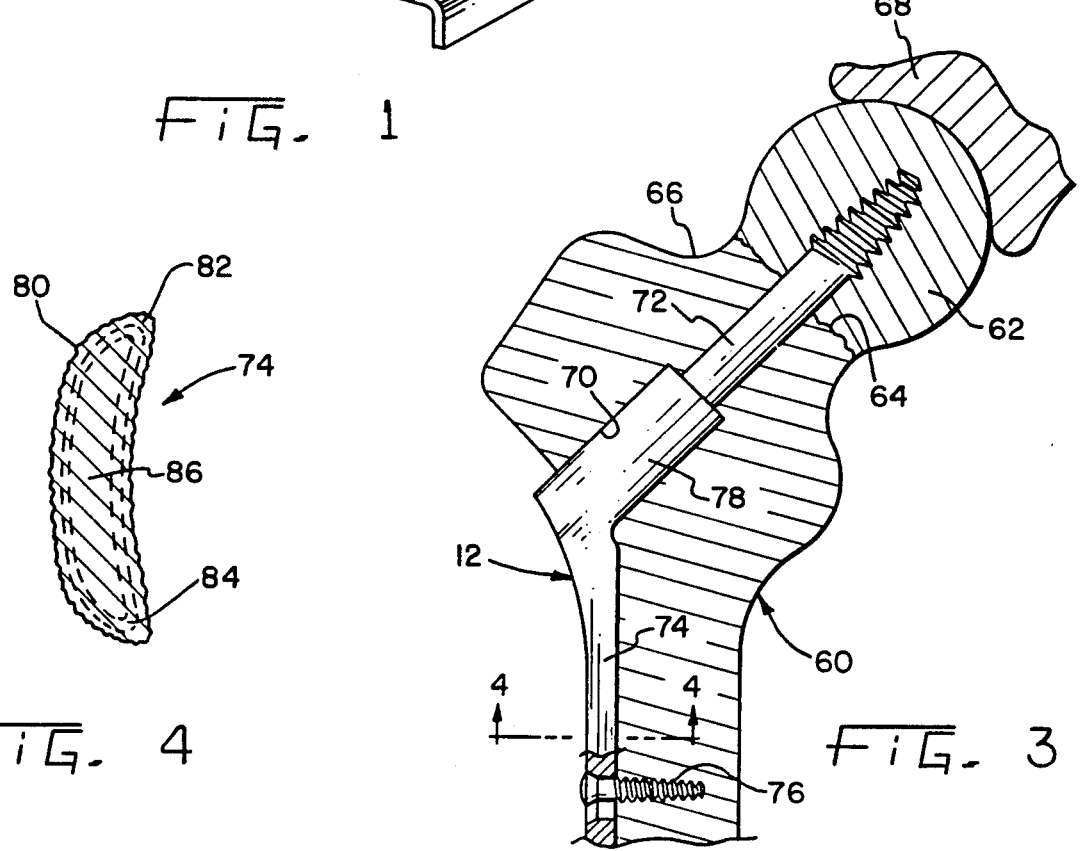

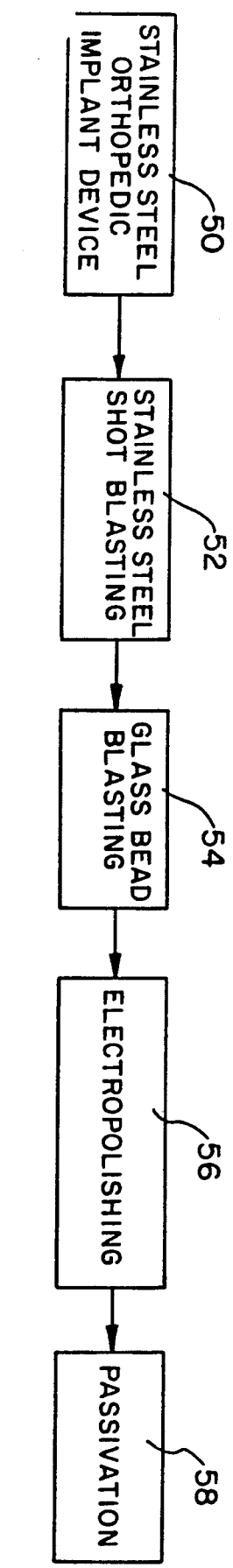

METHOD OF SURFACE FINISHING ORTHOPEDIC IMPLANT DEVICES

BACKGROUND OF THE INVENTION

The present invention relates generally to stainless steel orthopedic implant devices and, more particularly, to a surface treatment process applicable to such devices, wherein both the fatigue and corrosion properties of an orthopedic implant device are enhanced.

More specifically, the present invention relates to orthopedic implant devices commonly used by orthopedic surgeons to repair and replace fractured and deteriorating bones and joints. For example, U.S. Pat. No. 4,612,920, issued to Lower, discloses a compression hip screw of the general type to which the surface treatment process of the present invention is applicable. Other orthopedic devices that the present invention would be applicable to include, but are not limited to, hip prostheses, bone plates, intramedullary nails, and other fracture fixation devices fabricated from stainless steel.

Representative of the function of many orthopedic implant devices, the aforementioned compression hip screw rigidly connects a femoral head to the remaining portion of the femur despite a fracture in the area of the femur neck. During a normal walking cycle, substantial loads are imparted to and transferred by the compression hip screw. Consequently, it is desirable to reduce the possibility of a component failure that might require the patient to undergo further surgery.

A variety of stainless steel alloys are used for fracture fixation devices and are chosen on the basis of their high strength, ductility, fracture toughness, biocompatibility, and corrosion resistance. It is generally known that the fatigue and corrosion properties of orthopedic implant devices fabricated from these alloys can be affected by different surface treatment processes. For instance, one such process includes the steps of mechanical grinding, sisal buffing or color buffing, electropolishing, and passivation.

Recently, orthopedic implant devices have been surface treated by shot blasting with alumina, i.e., a form of aluminum oxide having a hard crystalline structure. Alumina is typically used as an abrasive and includes a sharp, irregular surface. Shot blasted alumina tends to become imbedded in and/or leave a residue on the surface of some stainless steels; therefore, subsequent steps of glass bead blasting and electropolishing are required.

While the surface finishing processes employed in the manufacture of stainless steel orthopedic implant devices have been generally successful in providing devices having clean surfaces, it is desired to develop a surface finishing process that maintains presently attained levels of surface cleanliness while further enhancing the fatigue properties of the device.

SUMMARY OF THE INVENTION

Generally, the present invention provides a process for surface finishing a stainless steel orthopedic implant device, wherein the fatigue strength of the device is greatly enhanced without compromising corrosion resistance properties of the stainless steel. The invention also encompasses orthopedic implant devices fabricated in accordance with the claimed process.

More specifically, the process of the present invention enhances the fatigue strength of a stainless steel implant device by causing a heavily cold-worked outer layer to be formed on the stainless steel implant device as the result of shot blasting with steel shot. A further step of the inventive process includes electropolishing the shot blasted surface.

In one aspect of the invention, the initial use of larger stainless steel shot and the subsequent use of smaller glass beads for shot blasting results in more thorough coverage and cold-working of the outer surface of a stainless steel orthopedic implant device. In another aspect of the invention, the step of electropolishing the cold-worked outer layer of the implant device is intended to restore corrosion resistance properties to the surface without diminishing gains in fatigue strength produced by the shot blasting steps of the process.

An advantage of the method of the present invention is that orthopedic implant devices having increased fatigue strength are possible as the result of surface treatment of the device.

Another advantage of the method of the present invention is that it is possible to significantly enhance the fatigue strength of an orthopedic implant devices without compromising corrosion resistance properties thereof.

A further advantage of the method of the present invention is that aluminum oxide contamination of the surface of stainless steel orthopedic implant devices is virtually eliminated.

Yet another advantage of the method of the present invention is that a stainless steel orthopedic implant device having a heavily cold-worked outer layer and a relatively soft center core may be easily fabricated, thereby providing a device exhibiting unique structural properties for orthopedic applications.

The invention, in one form thereof, provides a method of manufacturing an orthopedic implant device having enhanced fatigue properties. The method includes several essential steps, including an initial step of providing a metal substrate in the form of an orthopedic implant device, or component thereof. The metal substrate has a generally smooth outer surface which, pursuant to another step of the invention, is shot blasted with metal shot until a cold-worked outer layer is formed on the metal substrate. The cold-worked layer has a textured outer surface which, according to a further step of the invention, is electropolished. In one aspect of the invention according to this form, the textured outer surface is shot blasted with glass beads prior to electropolishing.

The invention further provides, in one form thereof, a method of increasing the fatigue strength of an orthopedic implant device that is fabricated from stainless steel. The outer surface of the device is first shot blasted with stainless steel shot. Next, the outer surface is shot blasted with glass bead shot having a nominal size less than the nominal size of the stainless steel shot. After shot blasting the outer surface with glass bead shot, electropolishing is performed on the outer surface. In one aspect of the invention according to this form thereof, the nominal size of the glass beads is preferably one-tenth to one-half that of the stainless steel shot.

BRIEF DESCRIPTION OF THE DRAWINGS

FIG. 1 is a perspective view of the spray nozzle and fixture associated with a bead blasting apparatus of the type used in accordance with the method of the present invention, wherein a fixation plate is shown being processed;

FIG. 2 is a diagrammatic representation of the process steps involved in an exemplary embodiment of the method of the present invention;

FIG. 3 is a fragmentary sectional view of a hip joint including a femur having a fracture at the neck thereof, wherein a compression hip screw, manufactured in accordance with the method of the present invention, is shown providing fixation of the femoral head to the femur; and FIG. 4 is an enlarged transverse sectional view of the plate of FIG. 3, taken along the line 4—4 in FIG. 3, particularly showing in exaggerated scale a textured outer surface, a heavily cold-worked outer layer, a less heavily cold-worked sublayer, and an unaffected inner core are in accordance with the present invention.

DESCRIPTION OF THE PREFERRED EMBODIMENT

Referring now to FIG. 1, there is shown a shot blasting nozzle and fixture assembly 10 of the type used in conjunction with a shot blasting apparatus (not shown) in carrying out the process and producing an orthopedic implant device 12 in accordance with the present invention. Assembly 10 includes a nozzle 14 used to carry and expel blasting media, i.e., stainless steel shot and glass beads, with high pressure air toward a target area of device 12. Nozzle 14 is connected to a hose 16, which is operably connected to a dry blast system, such as a Model 4228-F system manufactured by Cyclo-Blast Dry Honer Co. of Belmont, Ca.

Assembly 10 also includes a fixture 18 for supporting a workpiece, i.e., orthopedic implant device 12, during the shot blasting steps of the present invention, which steps will be more particularly described hereinafter. Fixture 18 includes a support block 20 attached to a base member 22 by means of a neck portion 24. As illustrated in FIG. 1, the top surface of support block 20 includes a V-shaped groove 26 in which device 12 is disposed during shot blasting operations. Nozzle 14 is selectively spaced above support block 20 by means of a horizontal plate member 28 having an opening 30 through which nozzle 14 is operably received and retained therein.

Plate member 28 is slidably connected to a vertical spacing bar 32, for selective positioning above support block 20, by means of a clamping block 34 and a pair of screws 36. Spacing bar 32 is fixedly mounted to support block 20 by a pair of screws 38. Accordingly, it can be seen from FIG. 1 that a nozzle opening 40 of nozzle 14, from which blasting media is expelled by high pressure air, is directed toward and selectively positioned above the workpiece resting on support block 20.

Referring now to FIG. 2, the steps for surface treating a stainless steel orthopedic implant device in accord with an exemplary embodiment of the present invention are diagrammatically illustrated. Generally, block 50 represents the first step of providing a stainless steel orthopedic implant device or a component part thereof, i.e., a metal substrate. Block 52 represents the next step of shot blasting the outer surface of the part with stainless steel shot. Block 54 represents the next step of shot blasting with glass beads. The part then undergoes electropolishing and passivation, as represented by blocks 56 and 58, respectively. The steps will now be described in detail.

The metal substrate provided in the step of block 50 is preferably hot forged or cold-worked 22Cr-13Ni-5Mn (22-13-5) stainless steel alloy (Rb 60 to Rc 50), or hot forged or cold-worked 316L stainless steel alloy (Rb 60 to Rc 50). Both are used in fracture fixation devices due to their high strength, ductility, fracture toughness, biocompatibility, and corrosion resistance. Inasmuch as the substrate has already been fabricated into an orthopedic implant component part prior to this step, the surface has been appropriately machined, surface ground, and/or mass tumbled.

The step of block 52 involves shot blasting the workpiece with stainless steel shot of a uniform size. In one embodiment, the shot used is cold-worked 304 stainless steel shot, the approximate uniform nominal size of which is selected to be either 0.0070, 0.0110, 0.0170, or 0.0280 inch, i.e., U.S. standard sieve sizes No. 80, No. 50, No. 40, and No. 25, respectively. More particularly, the shot originally consist of cylindrically-shaped particles which become spherically-shaped upon repeated use as a blasting medium. Stainless steel shot of the type disclosed herein is commercially available from Pellets, Inc. of Tonawanda, N.Y.

Although larger size shot is typically used on the cold-worked materials, the fatigue endurance limit of the treated stainless steel part has not been found to increase significantly with increased shot size. Essentially, shot blasting with steel shot increases the fatigue strength of the part by cold-working the outer surface layer, thereby introducing residual compressive stress on the surface.

As represented by the step of block 54, the workpiece may be shot blasted with glass beads, i.e., silicon oxide, after it has been shot blasted with stainless steel shot. The uniform nominal size of the glass beads used in the disclosed embodiment is approximately 0.0029 inch (U.S. standard sieve size No. 200) and, thus, is in the range of one-tenth to one-half the size of the steel shot previously described. Consequently, this step further improves the fatigue properties of the part by working the surface areas not covered by the larger steel shot. Additionally, the glass bead blasting helps clean the surface of any steel shot residue that may have been transferred to the target surface. Glass beads of the type disclosed herein are commercially available from Potters, Inc. of Cleveland, Ohio.

The steps of electropolishing and passivation, represented by blocks 56 and 58, respectively, are performed in accordance with conventional methods. Specifically, the electropolishing step is performed using 85% phosphoric acid to one part (by volume) of Electro-Glo 300 concentrate solution or equivalent, and the passivation step is performed using a nitric acid solution so as to provide a protective oxide film on the finished part. The electropolishing step is an important step in restoring the corrosion resistance properties of the surface and, therefore, should be controlled in such a way that it produces the desired results, i.e., cleaning and smoothening the surface and reducing stress concentration effects, without dissolving away the cold-worked surface layer produced during previous steps.

The corrosion properties of stainless steel orthopedic implant parts treated in accordance herewith are similar to that of the base alloys in a highly polished and passivated condition. Although shot blasting with steel shot deforms the surface and produces sharp corners that would ordinarily decrease corrosion resistance properties, glass bead blasting and electropolishing mechanically and electrochemically smoothen the surface and restore corrosion resistance properties thereto.

Referring now to FIGS. 3 and 4, a femur 60 is shown with a femoral head 62 and a fracture 64 located at a neck 66. Femoral head 62 forms a hip joint with an acetabular member 68. An opening 70 is formed in femur 60 to extend from a lateral side of the femur to an internal position within femoral head 62. In the disclosed embodiment of the present invention, orthopedic implant device 12 comprises a compression hip screw that has been treated according to the process of FIG. 2. Compression hip screw 12 is of the type disclosed in U.S. Pat. No. 4,612,920, assigned to the same assignee as the present invention, the disclosure of which is hereby incorporated by reference.

Generally, compression hip screw 12 includes a lag screw 72 threadedly secured to femoral head 62, a plate 74 adapted for attachment to the femur by means of bone screws 76, and a compression screw (not shown) for coupling lag screw 72 and plate 74. As shown in FIG. 3, an upper portion of plate 74 defines an integral barrel 78 disposed in opening 70, while a lower portion of the plate is attached to the lateral side of the femur.

Referring now to FIG. 4, a cross-sectional view of plate 74 of compression hip screw 12 illustrates the structure of a stainless steel orthopedic implant device in accordance with the present invention. Generally, shot blasting a stainless steel part with stainless steel shot, as described herein, results in a heavily cold-worked outer layer and a less heavily cold-worked sublayer (or diffused layer) having a thickness at least twice that of the outer layer. Specifically, FIG. 4 shows in exaggerated fashion a textured outer surface 80, a heavily cold-worked outer layer 82, a less heavily cold-worked sublayer 84, and an inner core or substrate 86 substantially unaffected by the surface treatment process described herein. In one embodiment, layer 82 is approximately 0.0035 to 0.0040 inches thick.

In a preferred embodiment of carrying out the process of the present invention, air pressure at 90–100 psi is used with the shot blasting apparatus to propel the steel shot, while air pressure at 40 psi is used for the glass bead blasting. All blasting is executed perpendicularly to the specimen surface, i.e., an angle of incidence of 90, at a distance of 1.5 and 2.0 inches from the tip of the nozzle. Parts machined from stainless steel are stress relieved prior to surface finishing.

The time duration for shot blasting with stainless steel shot to achieve thorough coverage of the target area varies according to several variables, including the type of shot and target materials, the size, shape, hardness, and density of the shot, and the velocity, flow rate, and angle of impact. However, for one exemplary shot blasting set-up, the fatigue strength increased rapidly over an elapsed time of approximately two minutes until a maximum fatigue strength was achieved at an optimal 100% surface coverage. Thereafter, the fatigue strength declined gradually. Accordingly, it is recommended that the duration be set at between 100–120% of the elapsed time experimentally determined to achieve 100% surface coverage, in order to minimize variances in fatigue strength for slightly different timed periods.

It will be appreciated that the fatigue strength of the surface finish produced by the process of the present invention is much more consistent than finishes of the prior art methods, due to the uniform shape and higher mass of steel shot and its ability to induce uniform cold-work on the surface of the alloy. It is noted that greater improvement of fatigue strength is typically experienced in the case of hot forged or annealed stainless steel. Lesser improvement will be experienced in cold-worked stainless steel, depending upon the alloy type and the degree of cold-working put into the alloy prior to being finished in accordance with the present invention.

It will be appreciated that the foregoing description of a preferred embodiment of the invention is presented by way of illustration only and not by way of any limitation, and that various alternatives and modifications may be made to the illustrated embodiment without departing from the spirit and scope of the invention.

We claim:

1. A method manufacturing an orthopaedic implant device having enhanced fatigue properties, comprising the steps of:
    providing a metal substrate in the form of an orthopaedic implant device with an outer surface;
    shot blasting said outer surface of said metal substrate with metal shot until a distinct cold-worked outer layer is formed on said metal substrate, said cold-worked layer having a textured outer surface;
    shot blasting said textured outer surface of said cold-worked outer layer with glass bead shot after shot blasting with metal shot is completed; and
    electropolishing said textured outer surface.

2. The method of claim 1 in which said steps of shot blasting with steel shot and shot blasting with glass beads are performed with steel shot and glass beads, respectively, wherein the nominal size of the glass beads is approximately 0.0029 inch and the nominal size of the steel shot is within the range of 0.0070 to 0.0280 inch.

3. The method of claim 1 in which said metal substrate is a stainless steel alloy.

4. The method of claim 3 in which said step of shot blasting with metal shot is performed using cold-worked stainless steel shot.

5. A method of increasing the fatigue strength of an orthopaedic implant device which has an outer surface, comprising the steps of:
    shot blasting the outer surface with a first shot having a first nominal size;
    after shot blasting the outer surface with the first shot, shot blasting the outer surface with a second shot having a second nominal size less than said first nominal size; and
    after shot blasting the outer surface with the second shot, electrpolishing the outer surface.

6. An orthopaedic implant device having enhanced fatigue properties, prepared by a process comprising the steps of:
    providing a metal substrate on the orthopaedic implant device, said metal substrate having a generally smooth outer surface;
    shot blasting said smooth outer surface of said metal substrate with metal shot until a distinct cold-worked outer layer is formed on said metal substrate, said cold-worked outer layer having a textured outer surface following said shot blasting;
    shot blasting said textured outer surface of said cold-worked outer layer with glass bead shot; and
    electropolishing said textured outer surface.

7. The orthopedic implant device of claim 6 in which said metal substrate is a stainless steel alloy.

8. The orthopedic implant device of claim 7 in which said metal substrate is 22-13-5 stainless steel.

9. The orthopedic implant device of claim 7 in which said metal substrate is 316L stainless steel.

* * * * *